(12) United States Patent
Arakawa

(10) Patent No.: US 11,984,136 B2
(45) Date of Patent: May 14, 2024

(54) EMOTION ESTIMATION APPARATUS, EMOTION ESTIMATION METHOD, AND COMPUTER READABLE RECORDING MEDIUM

(71) Applicant: NEC Corporation, Tokyo (JP)

(72) Inventor: Takayuki Arakawa, Tokyo (JP)

(73) Assignee: NEC CORPORATION, Tokyo (JP)

( * ) Notice: Subject to any disclaimer, the term of this patent is extended or adjusted under 35 U.S.C. 154(b) by 316 days.

(21) Appl. No.: 17/433,694

(22) PCT Filed: Feb. 28, 2019

(86) PCT No.: PCT/JP2019/007918
§ 371 (c)(1),
(2) Date: Aug. 25, 2021

(87) PCT Pub. No.: WO2020/174680
PCT Pub. Date: Sep. 3, 2020

(65) Prior Publication Data
US 2022/0148617 A1 May 12, 2022

(51) Int. Cl.
*G10L 25/63* (2013.01)
*A61B 5/00* (2006.01)
(Continued)

(52) U.S. Cl.
CPC ............. *G10L 25/63* (2013.01); *A61B 5/165* (2013.01); *A61B 5/4803* (2013.01); *G10L 25/18* (2013.01); *G10L 25/75* (2013.01)

(58) Field of Classification Search
CPC ......... G10L 25/18; G10L 25/63; G10L 25/75; A61B 5/165; A61B 5/4803
See application file for complete search history.

(56) References Cited

U.S. PATENT DOCUMENTS

2006/0183980 A1\* 8/2006 Yang ...................... G16H 20/60
128/920
2009/0318777 A1\* 12/2009 Kameyama ........ G01C 21/3608
704/251
(Continued)

FOREIGN PATENT DOCUMENTS

CN 1455916 A 11/2003
CN 108391207 A 8/2018
(Continued)

OTHER PUBLICATIONS

Yang Gao, Wei Wang, Vir V. Phoha, Wei Sun, and Zhanpeng Jin. "EarEcho: Using Ear Canal Echo for Wearable Authentication.", 2019, Proc. ACM Interact. Mob. Wearable Ubiquitous Technol. 3, 3, Article 81 (Sep. 2019), 24 pages. https://doi.org/10.1145/3351239 (Year: 2019).\*

(Continued)

*Primary Examiner* — Eric Yen

(57) ABSTRACT

An emotion estimation apparatus 1 includes: a generation unit 2 configured to generate acoustic characteristic information indicating an acoustic characteristic using a first acoustic signal output to the ear canal and a second acoustic signal produced by the first acoustic signal echoing inside the body; and an estimation unit 3 configured to estimate emotion using the acoustic characteristic information.

16 Claims, 10 Drawing Sheets

(51) Int. Cl.
*A61B 5/16* (2006.01)
*G10L 25/18* (2013.01)
*G10L 25/75* (2013.01)

(56) References Cited

U.S. PATENT DOCUMENTS

| | | | | |
|---|---|---|---|---|
| 2010/0328033 | A1* | 12/2010 | Kamei | G06V 40/12 |
| | | | | 340/5.82 |
| 2011/0040155 | A1* | 2/2011 | Guzak | G06F 3/0484 |
| | | | | 600/300 |
| 2012/0001846 | A1 | 1/2012 | Taniguchi et al. | |
| 2013/0336500 | A1 | 12/2013 | Sudo | |
| 2015/0032505 | A1 | 1/2015 | Kusukame et al. | |
| 2018/0114125 | A1 | 4/2018 | Ichiboshi et al. | |

FOREIGN PATENT DOCUMENTS

| | | |
|---|---|---|
| CN | 108594991 A | 9/2018 |
| CN | 109391870 A | 2/2019 |
| JP | 2006-071936 A | 3/2006 |
| JP | 2015-109964 A | 6/2015 |
| JP | 2018-072876 A | 5/2018 |
| JP | 2018-099239 A | 6/2018 |
| WO | 2010/090175 A1 | 8/2010 |
| WO | 2014/083778 A1 | 6/2014 |

OTHER PUBLICATIONS

Extended European Search Report for EP Application No. 19917143.0 dated Jan. 10, 2022.

Ha-Duong Bui et al., "An Integrated Approach to Human-Robot-Smart Environment Interaction Interface for Ambient Assisted Living", 2018 IEEE Workshop On Advanced Robotics and Its Social Impacts (ARSO), IEEE, Sep. 27, 2018, pp. 32-37.

International Search Report for PCT Application No. PCT/JP2019/007918, dated May 28, 2019.

Japanese Office Communication for JP Application No. 2021-501512 dated Jun. 28, 2022 with English Translation.

English translation of Written opinion for PCT Application No. PCT/JP2019/007918, dated May 28, 2019.

Chinese Office Action for CN Application No. 201980092989.4, mailed on Dec. 22, 2023 with English Translation.

\* cited by examiner

Fig.4

| Resonant Frequency Information |
|---|
| f1 |
| f2 |
| ⋮ |

| STATE ESTIMATION INFORMATION | | | |
|---|---|---|---|
| VOCAL TRACT STATE | WHETHER MOUTH IS OPEN OR CLOSED | OPEN | F11 |
| | | | F12 |
| | | | ⋮ |
| | | CLOSED | F21 |
| | | | F22 |
| | | | ⋮ |
| | WHETHER VOCAL CORDS ARE OPEN OR CLOSED | OPEN | F31 |
| | | | F32 |
| | | | ⋮ |
| | | CLOSED | F41 |
| | | | F42 |
| | | | ⋮ |
| | PLACE OF ARTICULATION | a | F51 |
| | | | F52 |
| | | | ⋮ |
| | | e, o | F61 |
| | | | F62 |
| | | | ⋮ |
| | | i | F71 |
| | | | F72 |
| | | | ⋮ |
| | | m, n | F71 |
| | | | F72 |
| | | | ⋮ |
| | | u | F81 |
| | | | F82 |
| | | | ⋮ |
| | | ⋮ | ⋮ |
| RESPIRATORY TRACT STATE | BREATHING TYPE | LUNG BREATHING | F81 |
| | | | F82 |
| | | | ⋮ |
| | | DIAPHRAGMATIC BREATHING | F91 |
| | | | F92 |
| | | | ⋮ |
| | ⋮ | | ⋮ |

| SPECTRAL SHAPE INFORMATION |
|---|
| sp1 |

52

| STATE ESTIMATION INFORMATION | | | |
|---|---|---|---|
| VOCAL TRACT STATE | WHETHER MOUTH IS OPEN OR CLOSED | OPEN | SP11 |
| | | CLOSED | SP12 |
| | WHETHER VOCAL CORDS ARE OPEN OR CLOSED | OPEN | SP21 |
| | | CLOSED | SP22 |
| | PLACE OF ARTICULATION | a | SP31 |
| | | e, o | SP32 |
| | | i | SP33 |
| | | m, n | SP34 |
| | | u | SP35 |
| | | ⋮ | ⋮ |
| RESPIRATORY TRACT STATE | BREATHING TYPE | LUNG BREATHING | SP41 |
| | | DIAPHRAGMATIC BREATHING | SP42 |
| | ⋮ | ⋮ | |

Fig.6
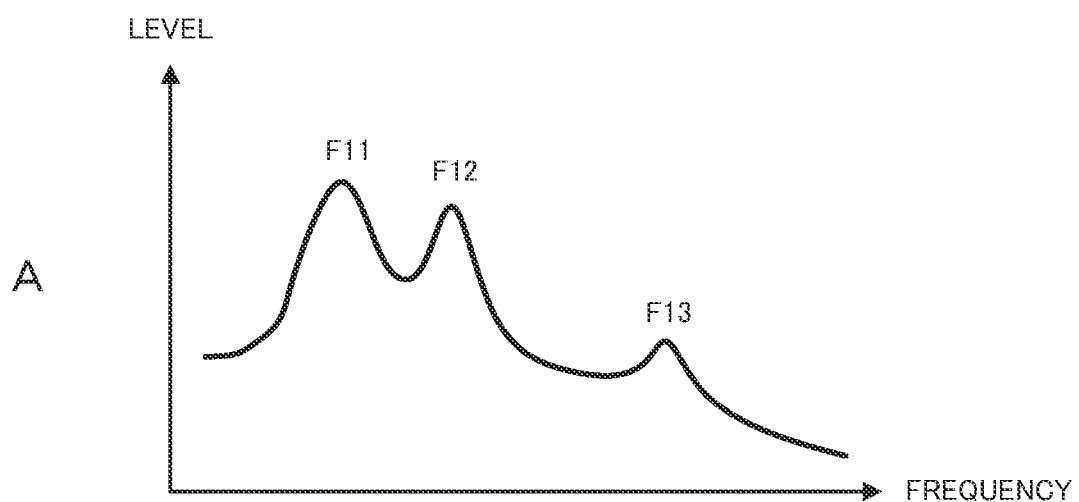
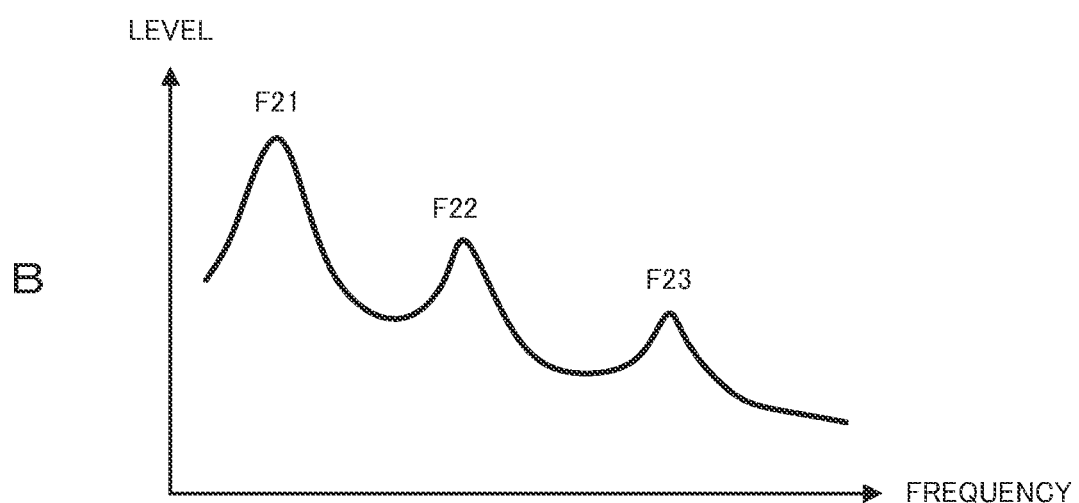

Fig.8

| EMOTION ESTIMATION INFORMATION | | | | | |
|---|---|---|---|---|---|
| EMOTION | WHETHER MOUTH IS OPEN OR CLOSED | WHETHER VOCAL CORDS ARE OPEN OR CLOSED | PLACE OF ARTICULATION | BREATHING TYPE | ... |
| PLEASURE | OPEN | OPEN | a | DIAPHRAGMATIC BREATHING | ... |
| SURPRISE | OPEN | OPEN | e, o | DIAPHRAGMATIC BREATHING | ... |
| ANGER | CLOSED | OPEN | i | LUNG BREATHING | ... |
| SADNESS | CLOSED | CLOSED | m, n | LUNG BREATHING | ... |
| SOBER FACE | CLOSED | CLOSED | u | LUNG BREATHING | ... |
| ⋮ | ⋮ | ⋮ | ⋮ | ⋮ | ⋮ |

81

EMOTION ESTIMATION APPARATUS, EMOTION ESTIMATION METHOD, AND COMPUTER READABLE RECORDING MEDIUM

This application is a National Stage Entry of PCT/JP2019/007918 filed on Feb. 28, 2019, the contents of all of which are incorporated herein by reference, in their entirety.

TECHNICAL FIELD

The disclosure relates to an emotion estimation apparatus and emotion estimation method for estimating emotion, and further relates to a computer readable recording medium that includes recorded thereon, a program for realizing the emotion estimation apparatus and emotion estimation method.

BACKGROUND ART

An apparatus is known for making communication smooth using a technique for estimating emotion. Such a technique for estimating emotion is used for smoothly performing conversation over telephone and conversation with a robot, for example.

As a related technique, Patent Document 1 discloses an apparatus that estimates user's emotion and supports conversation, using user's voice input through a microphone, an image in which user's expression is captured that is captured using an image capturing apparatus, and the like.

LIST OF RELATED ART DOCUMENTS

Patent Document

Patent Document 1: Japanese Patent Laid-Open Publication No. 2006-071936

SUMMARY

Technical Problems

However, in the apparatus disclosed in Patent Document 1 described above, user's voice is input using a microphone, and therefore the voice is likely to be influenced by noise such as environmental sound. Therefore, the accuracy in estimating emotion is degraded.

Therefore, the apparatus disclosed in Patent Document 1 estimates emotion by further combining an image in which user's expression is captured to the user's voice. However, the image is likely to be influenced by illumination and the like, and as a result, the accuracy in estimating emotion is degraded.

An example object of the disclosure is to provide an emotion estimation apparatus, an emotion estimation method, and a computer readable recording medium for improving the accuracy in estimating emotion.

Solution to the Problems

In order to achieve the above-described object, an emotion estimation apparatus according to an example aspect of the disclosure includes:

a generation unit configured to generate acoustic characteristic information indicating an acoustic characteristic using a first acoustic signal output to the ear canal and a second acoustic signal produced by the first acoustic signal echoing inside the body; and an estimation unit configured to estimate emotion using the acoustic characteristic information.

In addition, in order to achieve the above-described object, an emotion estimation method according to an example aspect of the disclosure includes:

(a) a step of generating acoustic characteristic information indicating an acoustic characteristic using a first acoustic signal output to the ear canal and a second acoustic signal produced by the first acoustic signal echoing inside the body; and (b) a step of estimating emotion using the acoustic characteristic information.

Furthermore, in order to achieve the above-described object, a computer readable recording medium that includes a program recorded thereon according to an example aspect of the disclosure includes recorded thereon, a program including instructions that cause a computer to carry out:

(a) a step of generating acoustic characteristic information indicating an acoustic characteristic using a first acoustic signal output to the ear canal and a second acoustic signal produced by the first acoustic signal echoing inside the body; and (b) a step of estimating emotion using the acoustic characteristic information.

Advantageous Effects of the Invention

As described above, according to the disclosure, the states of the vocal and respiratory tracts can be estimated easily.

BRIEF DESCRIPTION OF THE DRAWINGS

FIG. 4 is a diagram illustrating one example of data structures of resonant frequency information and state estimation information.

FIG. 5 is a diagram illustrating one example of data structures of spectral shape information and the state estimation information.

FIG. 6 is a diagram illustrating one example of resonant frequencies and spectral shapes included in the state estimation information.

FIG. 8 is a diagram illustrating an example of a data structure of emotion estimation information of a modification.

EXAMPLE EMBODIMENT

Example Embodiment

In the following, an example embodiment of the invention disclosure will be described with reference to FIGS. 1 to 10.

[Apparatus Configuration]

Figure 1:
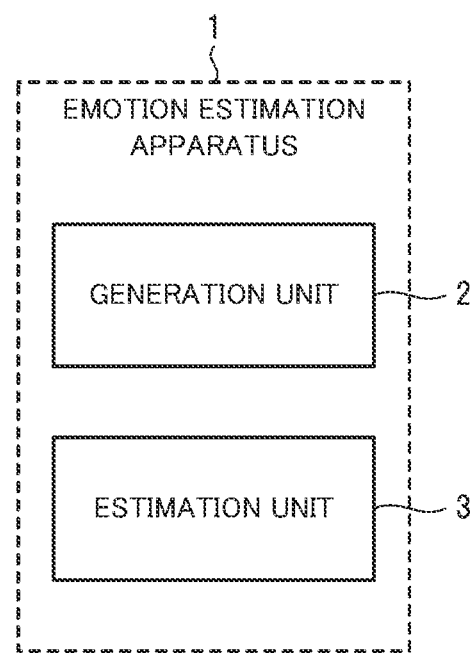
FIG. 1 is a diagram illustrating one example of an emotion estimation apparatus.

First, a configuration of an emotion estimation apparatus 1 in the example embodiment will be described with reference to FIG. 1. FIG. 1 is a diagram illustrating one example of the emotion estimation apparatus.

The emotion estimation apparatus illustrated in FIG. 1 is an apparatus for improving the accuracy in estimating emotion. Furthermore, as illustrated in FIG. 1, the emotion estimation apparatus 1 includes a generation unit 2 and an estimation unit 3.

Of the two units, the generation unit 2 generates acoustic characteristic information indicating an acoustic characteristic using an acoustic signal (first acoustic signal) output to the ear canal and an echo signal (second acoustic signal) produced by the acoustic signal echoing inside the body. The estimation unit 3 estimates emotion using the acoustic characteristic information.

In such a manner, in the example embodiment, acoustic characteristic information such as an impulse response h(t) or a transfer function H(ω) or H(z) is generated using an acoustic signal x(t) output to the ear canal of a target user and an echo signal y(t) reflecting the states of organs inside the body. Thus, since the states of organs inside the body can be estimated from the acoustic characteristic information, the emotion of a subject can be accurately estimated.

[System Configuration]

Figure 2:
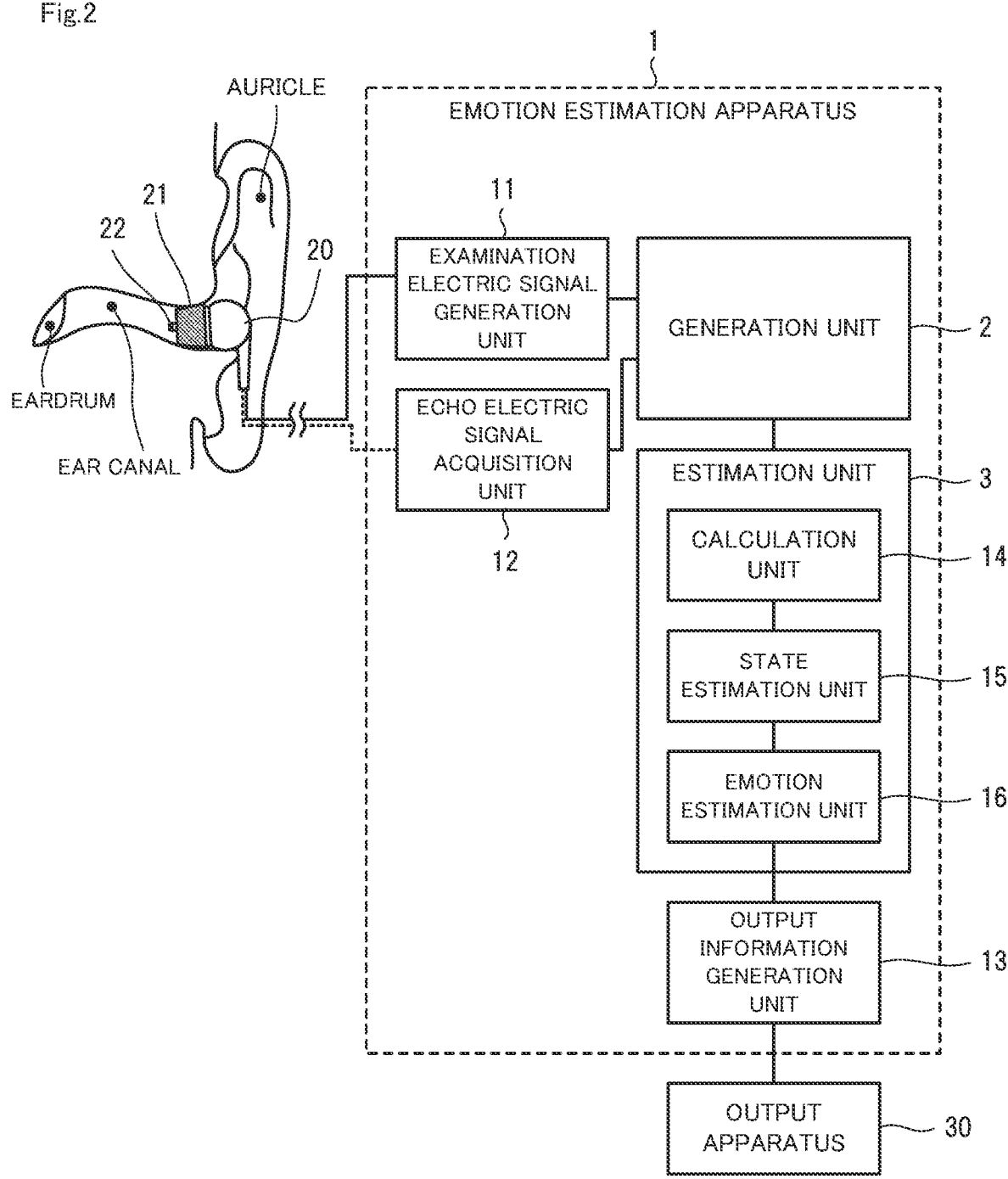
FIG. 2 is a diagram illustrating one example of a system including the emotion estimation apparatus.

Next, the configuration of the emotion estimation apparatus 1 in the example embodiment will be described in detail with reference to FIG. 2. FIG. 2 is a diagram illustrating one example of a system including the emotion estimation apparatus.

As illustrated in FIG. 2, the system in the example embodiment includes an ear-mounted apparatus 20 and an output apparatus 30, in addition to the emotion estimation apparatus 1. Furthermore, the emotion estimation apparatus 1 includes an examination electric signal generation unit 11, an echo electric signal acquisition unit 12, and an output information generation unit 13, in addition to the generation unit 2 and the estimation unit 3. Furthermore, the estimation unit 3 includes a calculation unit 14, a state estimation unit 15, and an emotion estimation unit 16. The ear-mounted apparatus 20 includes an examination sound signal reproduction unit 21 and an echo sound signal recording unit 22.

The ear-mounted apparatus 20 includes the examination sound signal reproduction unit 21, which is for outputting an acoustic signal to the ear canal, and the echo sound signal recording unit 22, which is for receiving input of (measuring) an echo signal in the ear canal. Specifically, the ear-mounted apparatus 20 is an apparatus that is used in a state in which the ear-mounted apparatus 20 is worn in the ear canal, as illustrated in the cross-sectional diagram of the outer ear (diagram illustrating the auricle, ear canal, and eardrum) in FIG. 2. For example, an earphone provided with a microphone is conceivable as the ear-mounted apparatus 20.

Note that the configuration of the ear-mounted apparatus 20 is not limited to that illustrated in FIG. 2, and any configuration may be adopted as long as an echo signal corresponding to an acoustic signal can be measured.

Upon receiving an electric signal generated by the examination electric signal generation unit 11 that corresponds to an acoustic signal, the examination sound signal reproduction unit 21 (acoustic signal output unit) generates the acoustic signal based on the received electric signal and outputs the generated acoustic signal to the ear canal. Note that a speaker or the like, for example, is conceivable as the examination sound signal reproduction unit 21.

Upon receiving an echo signal corresponding to the acoustic signal output from the examination electric signal generation unit 11, the echo sound signal recording unit 22 (acoustic signal input unit) converts the echo signal into an electric signal and transmits the electric signal to the echo electric signal acquisition unit 12. Note that a microphone or the like, for example, is conceivable as the echo sound signal recording unit 22.

The output apparatus 30 acquires the later-described output information, which has been converted into an outputtable format by the output information generation unit 13, and outputs images, sounds, etc., generated based on the output information. The output apparatus 30 is an image display device, etc., in which liquid crystal, organic electroluminescence (EL), or a cathode ray tube (CRT) is used, for example. Furthermore, the image display device may include a sound output device such as a speaker. Note that the output apparatus 30 may be a printing device such as a printer.

The examination electric signal generation unit 11 generates the electric signal used to output the acoustic signal, and transmits the electric signal to the examination sound signal reproduction unit 21. Specifically, the examination electric signal generation unit 11 generates, as the electric signal corresponding to the acoustic signal, a maximal length sequence (M-sequence) signal, a time-stretched pulse (TSP) signal, a Log-TSP signal, or the like. Furthermore, the examination electric signal generation unit 11 transmits the electric signal corresponding to the acoustic signal to the generation unit 2.

Note that a sweep signal, music, audio guidance, etc., may be included in the acoustic signal. Furthermore, the frequencies used for the acoustic signal are set in accordance with target organs. For example, when the vocal and respiratory tracts, etc., are set as targets, the frequency band of the acoustic signal is preferably set to 100-4 k [Hz]. However, there is no limitation to this frequency band.

Here, the vocal tract (articulatory organs), for example, is a path of voice, and is a cavity in the body through which sound produced by the vocal cords passes before being emitted to the outside of the body. The respiratory tract (phonatory organs), for example, is a path of respiratory sound and is involved in external respiration. The respiratory tract is formed from the upper respiratory tract (the nasal cavity, the pharynx, the larynx, etc.) and the lower respiratory tract (the trachea, the primary bronchi, the lungs, etc.).

The echo electric signal acquisition unit 12 receives the electric signal corresponding to the echo signal from the echo sound signal recording unit 22, adjusts the received electric signal, and transmits the adjusted electric signal to the generation unit 2. Specifically, the echo electric signal acquisition unit 12 adjusts the received electric signal using a circuit including a filter, an amplifier, etc., and transmits the adjusted electric signal to the generation unit 2.

The generation unit 2 generates acoustic characteristic information indicating an acoustic characteristic using an electric signal corresponding to an acoustic signal x(t) and an electric signal corresponding to an echo signal y(t). For example, an impulse response h(t), a transfer function H(ω) or H(z) obtained by performing Fourier transform or Laplace transform on the impulse response, or the like is used as the acoustic characteristic.

Specifically, the generation unit 2 first receives the electric signal corresponding to the acoustic signal x(t) from the examination electric signal generation unit 11. Furthermore, the generation unit 2 receives the electric signal corresponding to the echo signal y(t) from the echo electric signal acquisition unit 12. Subsequently, the generation unit 2 generates the acoustic characteristic information (an impulse response h(t), a transfer function H(ω) or H(z), or the like)

based on the received electric signals corresponding to the acoustic signal x(t) and the echo signal y(t).

Subsequently, the generation unit 2 stores the acoustic characteristic information to a storage unit, which is not illustrated. Note that the storage unit may be provided inside or outside the emotion estimation apparatus 1.

Since the echo signal y(t) reflects changes (changes in reflection ratio, attenuation rate, etc.) that are in accordance with the states of the subject's organs, information relating to the states of organs inside the body can be extracted by generating the acoustic characteristic information, which is an impulse response h(t), a transfer function H($\omega$) or H(z), or the like. Also, the echo signal includes an acoustic signal coming back from spaces (the ear canal, and the vocal and respiratory tracts) located between the head and the lungs, for example. Note that the reflection ratio is the ratio of the reflection to the input, and the attenuation rate is the rate of attenuation per unit time or unit cycle.

The estimation unit 3 estimates emotion using the acoustic characteristic information. Specifically, the estimation unit 3 estimates the state of the vocal tract and the state of the respiratory tract using the acoustic characteristic information, and estimates emotion using the estimated states of the vocal tract and the respiratory tract. Note that the estimation unit 3 estimates at least one or more states among whether the mouth is open or closed, whether the vocal cords are open or closed, the place of articulation, and the breathing type (lung breathing, diaphragmatic breathing, etc.), and sets the states as the state of the vocal tract and the state of the respiratory tract.

The estimation unit 3 (calculation unit 14, state estimation unit 15, emotion estimation unit 16) will be described in detail.

Using the acoustic characteristic information, the calculation unit 14 calculates resonant frequency information including information indicating resonant frequencies (frequencies with peak values in frequency characteristics), or spectral shape information indicating a spectral shape.

Figure 3:
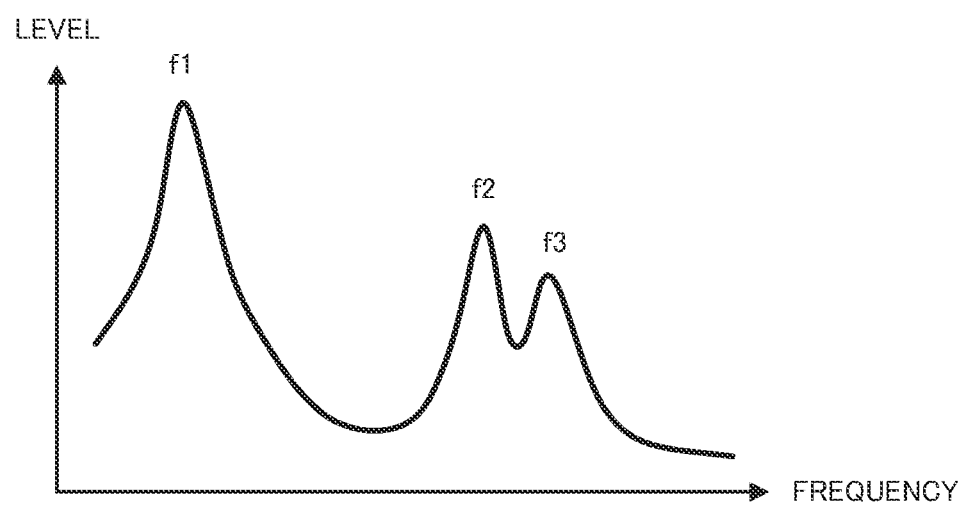
FIG. 3 is a diagram illustrating one example of resonant frequencies and a spectral shape.

FIG. 3 is a diagram illustrating one example of resonant frequencies and a spectral shape. FIG. 3 illustrates resonant frequencies f1, f2, and f3 included in resonant frequency information, and a spectral shape included in spectral shape information.

The calculation of resonant frequencies will be described.

The calculation unit 14 first acquires the acoustic characteristic information from the generation unit 2. Subsequently, the calculation unit 14 performs spectral analysis using the acoustic characteristic, and calculates resonant frequencies for the subject. The calculation unit 14 calculates resonant frequencies using linear predictive coding (LPC), etc., as the spectral analysis, for example. Then, the calculation unit 14 generates resonant frequency information indicating the resonant frequencies, and stores the generated resonant frequency information to the storage unit. Note that the method for calculating resonant frequencies is not limited to LPC, and any method may be used as long as resonant frequencies can be calculated.

The calculation of a spectral shape will be described.

The calculation unit 14 first acquires the acoustic characteristic information from the generation unit 2. Subsequently, the calculation unit 14 performs spectral analysis using the acoustic characteristic, and calculates a spectral shape (spectral envelope) for the subject. The calculation unit 14 calculates a spectral shape using cepstrum analysis, etc., as the spectral analysis, for example. Then, the calculation unit 14 generates spectral shape information indicating the spectral shape, and stores the generated spectral shape information to the storage unit.

The state estimation unit 15 estimates the states of the subject's organs using the generated resonant frequency information or spectral shape information. Specifically, the state estimation unit 15 first acquires the generated resonant frequency information or spectral shape information.

Subsequently, the state estimation unit 15 estimates the states of the subject's organs by using the resonant frequency information or spectral shape information and referring to state estimation information stored in advance. For example, the states of organs are the state of the vocal tract, the state of the respiratory tract, etc.

Note that, as the state of the vocal tract, states such as whether the mouth is open or closed, whether the vocal cords are open or closed, and the place of articulation are conceivable, for example. As the state of the respiratory tract, breathing type is conceivable, for example.

In regard to whether the mouth is open or closed, if the mouth is open, the sound pressure at low frequencies decreases since the pressure inside the mouth decreases. Furthermore, when the mouth is opened and closed, resonant frequencies change since the open and closed ends in the air column resonance model change.

In regard to whether the vocal cords are open or closed, the air column length changes when the vocal cords (glottis) are opened and closed. For example, the air column length from the mouth to the vocal cords or the air column length from the mouth to the lungs changes.

In regard to the place of articulation, the spectral shape and the formant frequencies including the resonant frequencies change when the positions of the tongue and teeth change.

In regard to breathing type, the size of the respiratory tract changes depending upon whether lung breathing (the lungs contract) or diaphragmatic breathing (the diaphragm moves up and down) is being performed.

Subsequently, the state estimation unit 15 generates state information indicating the states of the organs, and stores the state information to the storage unit. For example, the state information includes information indicating the state of the vocal tract and the state of the respiratory tract. For example, the state of the vocal tract includes information indicating states such as whether the mouth is open or closed, whether the vocal cords are open or closed, the place of articulation, etc. Furthermore, the state of the respiratory tract includes information indicating breathing type, for example.

A case in which resonant frequencies are used will be described.

The state estimation unit 15 first acquires the resonant frequency information generated by the calculation unit 14. Subsequently, the state estimation unit 15 calculates distances using the resonant frequency information and the state estimation information illustrated in FIG. 4, and estimates the states of the organs using the calculated distances.

FIG. 4 is a diagram illustrating one example of data structures of the resonant frequency information and the state estimation information. For example, in a case in which the state estimation unit 15 estimates whether the mouth is open or closed, the state estimation unit 15 uses a feature amount characterized by resonant frequencies f1, f2, . . . included in resonant frequency information 41 and calculates the distance to a feature amount characterized by resonant frequencies F11, F12, . . . corresponding to "OPEN" included in "WHETHER MOUTH IS OPEN OR CLOSED" included in state estimation information 42 and the distance to a feature amount characterized by resonant frequencies F21, F22, . . . corresponding to "CLOSED" included in "WHETHER MOUTH IS OPEN OR CLOSED" included in the state estimation information 42.

Furthermore, the state estimation unit 15 selects the closer one of the feature amounts and sets the state corresponding to the selected feature amount as the state as to whether the mouth is open or closed. Similarly, the state estimation unit 15 performs the estimation of state also with regard to whether or not the vocal cords are open or closed, the place of articulation (the sounds "a", "e, o", "i", "m, n", and "u", etc.), and breathing type (lung breathing, diaphragmatic breathing). Subsequently, the state estimation unit 15 generates state information indicating the states of the organs, and stores the state information to the storage unit.

A case in which spectral shapes are used will be described.

The state estimation unit 15 first acquires the spectral shape information generated by the calculation unit 14. Subsequently, the state estimation unit 15 calculates distances using the spectral shape information and the state estimation information illustrated in FIG. 5, and estimates the states of the organs using the calculated distances.

FIG. 5 is a diagram illustrating one example of data structures of the spectral shape information and the state estimation information. For example, in a case in which the state estimation unit 15 estimates whether the mouth is open or closed, the state estimation unit 15 uses a feature amount characterized by information sp1 indicating a spectral shape included in spectral shape information 51 and calculates the distance to a feature amount characterized by a spectral shape SP11 corresponding to "OPEN" included in "WHETHER MOUTH IS OPEN OR CLOSED" included in state estimation information 52 and the distance to a feature amount characterized by a spectral shape SP21 corresponding to "CLOSED" included in "WHETHER MOUTH IS OPEN OR CLOSED" included in the state estimation information 52.

FIG. 6 is a diagram illustrating one example of resonant frequencies and spectral shapes included in the state estimation information. The spectral shapes shown in portions A and B of FIG. 6 correspond to the spectral shapes SP11 and SP12 illustrated in FIG. 5, for example.

Then, the state estimation unit 15 selects the state corresponding to the closer one of the feature amounts and sets the state as the state as to whether the mouth is open or closed. Similarly, the state estimation unit 15 performs the estimation of state also with regard to whether or not the vocal cords are open or closed, the place of articulation (the sounds "a", "e, o", "i", "m, n", and "u", etc.), and breathing type (lung breathing, diaphragmatic breathing). Subsequently, the state estimation unit 15 generates state information indicating the states of the organs, and stores the state information to the storage unit.

The emotion estimation unit 16 estimates emotion using the estimated states of the vocal tract and the respiratory tract. Specifically, the emotion estimation unit 16 first acquires state information from the state estimation unit 15. Next, the emotion estimation unit 16 estimates emotion by referring to the emotion estimation information using the state information. Thereafter, the emotion estimation unit 16 transmits information indicating the estimated emotion to the output information generation unit 13.

Figure 7:
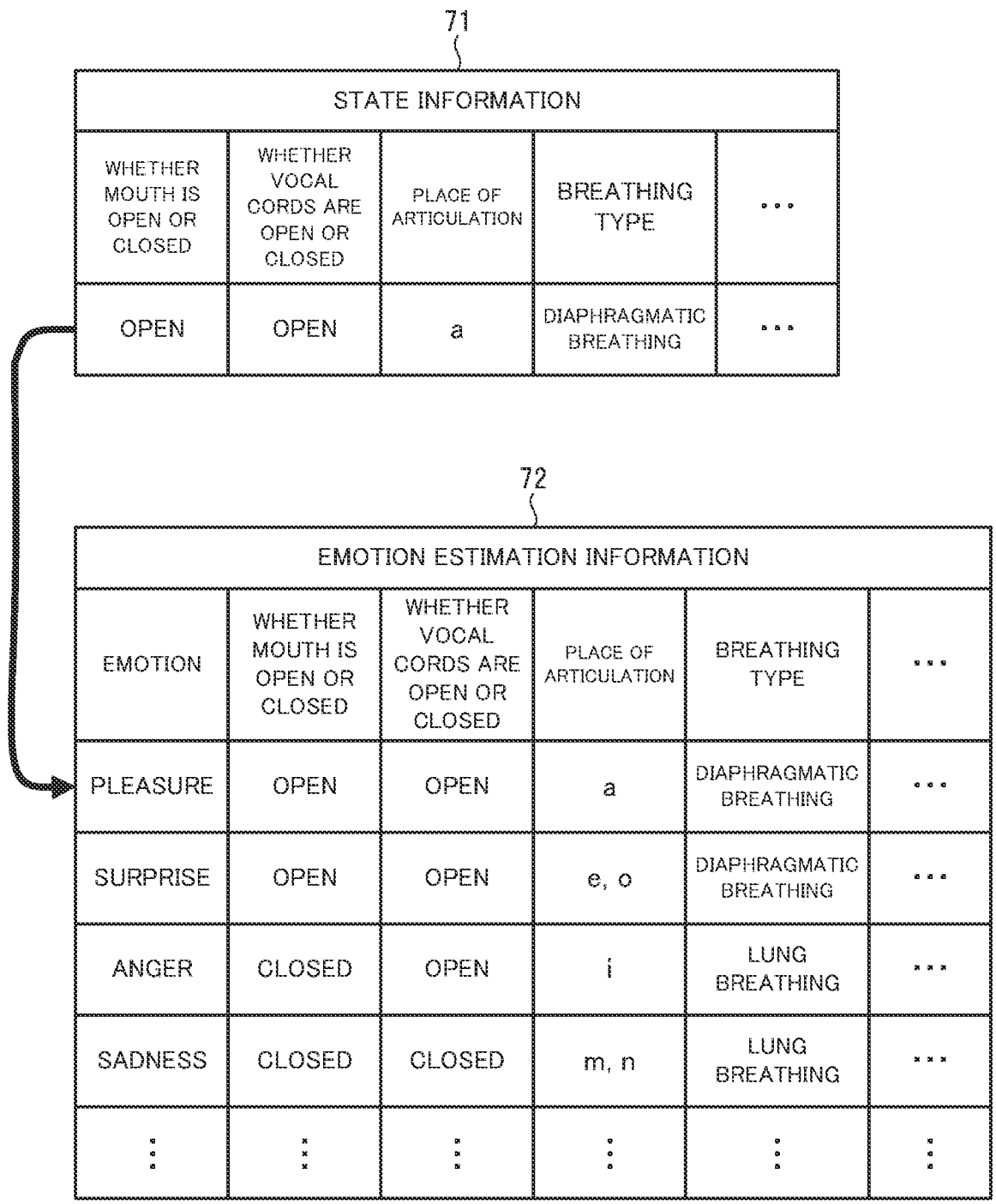
FIG. 7 is a diagram illustrating an example of data structures of state information and emotion estimation information.

FIG. 7 is a diagram illustrating an example of data structures of state information and emotion estimation information. For example, when the state information 71 includes information regarding whether the mouth is open or closed, whether the vocal cords are open or closed, the place of articulation, the state of the respiratory tract, and the breathing type, as shown in FIG. 7, the emotion estimation unit 16 selects the emotion by referring to the emotion estimation information 72. In the example in FIG. 7, "pleasure" is selected as the emotion.

Also, the emotion estimation unit 16 may estimate the emotion using a function generated using multi-variable analysis such as principal component analysis or multiple regression analysis.

In a case of principal component analysis, each piece of information included in the state information is used as a variable, each emotion is used as a principal component (synthetic variable), and a function is generated using weighting that is determined such that the synthetic variables include information (variance) of original variables as much as possible, for example. Then, the emotion estimation unit 16 estimates the emotion using the generated function.

In a case of multiple regression analysis, a regression formula is generated using each piece of information included in the state information as an explanatory variable, and using each emotion as an objective variable, for example. Then, the emotion estimation unit 16 estimates the emotion using the generated regression formula.

Moreover, the emotion estimation unit 16 may also estimate the emotion using SVM (Support Vector Machine). Specifically, the emotion estimation unit 16 is applied with a learning model for identifying the emotion, and estimates the emotion using the state information as an input. For example, the emotion estimation unit 16 estimates the emotion by inputting estimated items indicating whether the mouth is open or closed, whether the vocal cords are open or closed, the place of articulation, the state of the respiratory tract, the breathing type, and the like to the learning model.

Note that the learning model is generated by performing learning using supervised data in a learning phase, in advance.

Also, a learning model generated based on machine learning other than SVM may also be applied to the emotion estimation unit 16. For example, it is conceivable to use a neural network or a decision tree as the machine learning other than SVM.

Moreover, the estimation unit 3 may also estimate the state of the vocal tract and the state of the respiratory tract using the acoustic characteristic information, and estimate the face expression of a subject using the estimated states of the vocal tract and the respiratory tract. In this case, a face expression such as "sober face" is added, as shown in FIG. 8. FIG. 8 is a diagram illustrating an example of a data structure of emotion estimation information of a modification.

Upon acquiring the information indicating emotion from the emotion estimation unit 16, the output information generation unit 13 generates output information based on the information and transmits the output information to the output apparatus 30. The output apparatus 30 outputs the emotion of the subject based on the output information.

[Apparatus Operations]

Figure 9:
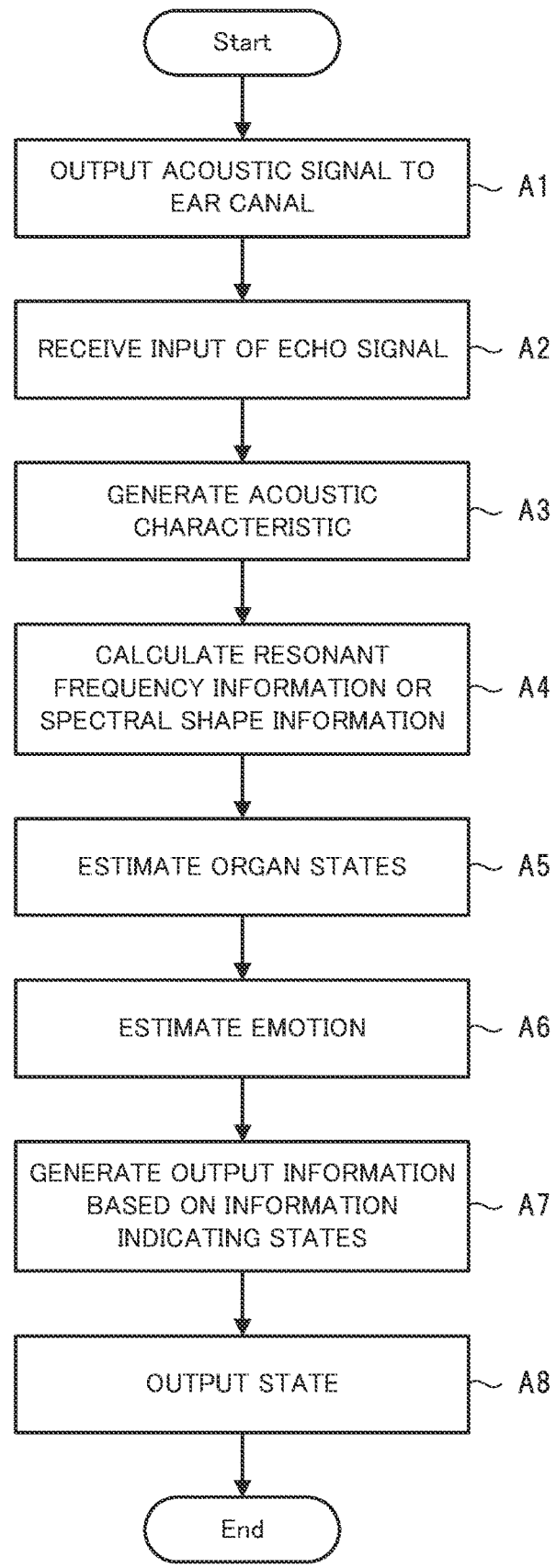
FIG. 9 is a diagram illustrating one example of operations of the emotion estimation apparatus.

Next, operations of the emotion estimation apparatus in the example embodiment of the disclosure will be described with reference to FIG. 9. FIG. 9 is a diagram illustrating one example of operations of the emotion estimation apparatus. FIGS. 2 to 8 will be referred to as needed in the following description. Furthermore, in the example embodiment, an emotion estimation method is implemented by causing the emotion estimation apparatus to operate. Accordingly, the following description of the operations of the emotion estimation apparatus is substituted for the description of the emotion estimation method in the example embodiment.

As illustrated in FIG. 9, first, upon receiving an electric signal that corresponds to an acoustic signal and that is generated by the examination electric signal generation unit 11, the examination sound signal reproduction unit 21 generates the acoustic signal based on the received electric signal and outputs the generated acoustic signal to the ear canal (step A1).

Subsequently, the echo sound signal recording unit 22 receives input of (measures) an echo signal corresponding to the acoustic signal output from the examination electric signal generation unit 11 (step A2). Then, the echo sound signal recording unit 22 converts the received echo signal into an electric signal and transmits the electric signal to the echo electric signal acquisition unit 12.

Subsequently, the generation unit 2 generates acoustic characteristic information indicating an acoustic characteristic using the electric signal corresponding to the acoustic signal x(t) and the electric signal corresponding to the echo signal y(t) (step A3). For example, an impulse response h(t), a transfer function H(ω) or H(z) obtained by performing Fourier transform or Laplace transform on the impulse response, or the like is used as the acoustic characteristic.

Specifically, in step A3, the generation unit 2 first receives the electric signal corresponding to the acoustic signal x(t) from the examination electric signal generation unit 11. Furthermore, the generation unit 2 receives the electric signal corresponding to the echo signal y(t) from the echo electric signal acquisition unit 12.

Subsequently, in step A3, the generation unit 2 generates the acoustic characteristic information (an impulse response h(t), a transfer function H(ω) or H(z), or the like) based on the received electric signals corresponding to the acoustic signal x(t) and the echo signal y(t). Furthermore, in step A3, the generation unit 2 stores the acoustic characteristic information to the storage unit, which is not illustrated.

Subsequently, the calculation unit 14 calculates resonant frequency information including information indicating resonant frequencies or spectral shape information indicating a spectral shape using the acoustic characteristic information (step A4).

The calculation of resonant frequencies in step A4 will be described.

In step A4, the calculation unit 14 first acquires the acoustic characteristic information from the generation unit 2. Subsequently, the calculation unit 14 performs spectral analysis using the acoustic characteristic, and calculates resonant frequencies for the subject. The calculation unit 14 calculates resonant frequencies using linear predictive coding (LPC), etc., as the spectral analysis, for example. Then, in step A4, the calculation unit 14 generates resonant frequency information indicating the resonant frequencies, and stores the generated resonant frequency information to the storage unit.

The calculation of a spectral shape in step A4 will be described.

In step A4, the calculation unit 14 first acquires the acoustic characteristic information from the generation unit 2. Subsequently, the calculation unit 14 performs spectral analysis using the acoustic characteristic, and calculates a spectral shape (spectral envelope) for the subject. The calculation unit 14 calculates a spectral shape using cepstrum analysis, etc., as the spectral analysis, for example. Then, in step A4, the calculation unit 14 generates spectral shape information indicating the spectral shape, and stores the generated spectral shape information to the storage unit.

Subsequently, the state estimation unit 15 estimates the states of the subject's organs using the generated resonant frequency information or spectral shape information (step A5). Specifically, in step A5, the state estimation unit 15 first acquires the generated resonant frequency information or spectral shape information.

Subsequently, in step A5, the state estimation unit 15 estimates the states of the subject's organs by using the resonant frequency information or spectral shape information and referring to state estimation information stored in advance.

Subsequently, in step A5, the state estimation unit 15 generates state information indicating the states of the organs, and stores the state information to the storage unit. For example, the state information includes information indicating the state of the vocal tract and the state of the respiratory tract. For example, the state of the vocal tract includes information indicating states such as whether the mouth is open or closed, whether the vocal cords are open or closed, the place of articulation, etc. Furthermore, the state of the respiratory tract includes information indicating breathing type, for example.

A case in which estimation is performed using resonant frequencies will be described.

In step A5, the state estimation unit 15 first acquires the resonant frequency information generated by the calculation unit 14. Subsequently, in step A5, the state estimation unit 15 calculates distances using the resonant frequency information and the state estimation information illustrated in FIG. 4, and estimates the states of the organs using the calculated distances.

For example, in a case in which the state estimation unit 15 estimates whether the mouth is open or closed, the state estimation unit 15 uses a feature amount characterized by resonant frequencies f1, f2, . . . included in resonant frequency information 41 and calculates the distance to a feature amount characterized by resonant frequencies F11, F12, . . . corresponding to "OPEN" included in "WHETHER MOUTH IS OPEN OR CLOSED" included in state estimation information 42 and the distance to a feature amount characterized by resonant frequencies F21, F22, . . . corresponding to "CLOSED" included in "WHETHER MOUTH IS OPEN OR CLOSED" included in the state estimation information 42.

Then, in step A5 the state estimation unit 15 selects the closer one of the feature amounts and sets the state corresponding to the selected feature amount as the state as to whether the mouth is open or closed. Similarly, the state estimation unit 15 performs the estimation of state also with regard to whether or not the vocal cords are open or closed, the place of articulation (the sounds "a", "e, o", "i", "m, n", and "u", etc.), and breathing type (lung breathing, diaphragmatic breathing). Subsequently, the state estimation unit 15 generates state information indicating the states of the organs, and stores the state information to the storage unit.

A case in which estimation is performed using a spectral shape will be described.

In step 5, the state estimation unit 15 first acquires the spectral shape information generated by the calculation unit 14. Subsequently, in step 5, the state estimation unit 15 calculates distances using the spectral shape information and the state estimation information illustrated in FIG. 5, and estimates the states of the organs using the calculated distances.

For example, in a case in which the state estimation unit 15 estimates whether the mouth is open or closed, the state estimation unit 15 uses a feature amount characterized by information sp1 indicating a spectral shape included in spectral shape information 51 and calculates the distance to a feature amount characterized by a spectral shape SP11 corresponding to "OPEN" included in "WHETHER MOUTH IS OPEN OR CLOSED" included in state estimation information 52 and the distance to a feature amount characterized by a spectral shape SP21 corresponding to "CLOSED" included in "WHETHER MOUTH IS OPEN OR CLOSED" included in the state estimation information 52.

Then, in step 5, the state estimation unit 15 selects the state corresponding to the closer one of the feature amounts and sets the state as the state as to whether the mouth is open or closed. Similarly, the state estimation unit 15 performs the estimation of state also with regard to whether or not the vocal cords are open or closed, the place of articulation (the sounds "a", "e, o", "i", "m, n", and "u", etc.), and breathing type (lung breathing, diaphragmatic breathing). Subsequently, the state estimation unit 15 generates state information indicating the states of the organs, and stores the state information to the storage unit.

Next, the emotion estimation unit 16 estimates the emotion using the estimated states of the vocal tract and the respiratory tract (step A6). Specifically, in step A6, the emotion estimation unit 16 first acquires state information from the state estimation unit 15. Next, in step A6, the emotion estimation unit 16 estimates the emotion by referring to the emotion estimation information using the state information. Thereafter, in step A6, the state estimation unit 15 transmits information indicating the estimated emotion to the output information generation unit 13.

For example, when the state information 71 includes information indicating whether the mouth is open or closed, whether the vocal cords are open or closed, the place of articulation, the state of the respiratory tract, and the breathing type, as shown in FIG. 7, the emotion estimation unit 16 selects the emotion by referring to the emotion estimation information 72. In the example in FIG. 7, "pleasure" is selected as the emotion.

Also, in step A6, the emotion estimation unit 16 may also estimate the emotion using a function generated using multi-variable analysis such as principal component analysis or multiple regression analysis.

Moreover, the emotion estimation unit 16 may estimate the emotion using SVM. Specifically, the emotion estimation unit 16 is applied with a learning model for identifying emotion, and estimates the emotion using the state information as an input. For example, the emotion estimation unit 16 estimates the emotion by inputting estimated items indicating whether the mouth is open or closed, whether the vocal cords are open or closed, the place of articulation, the state of the respiratory tract, the breathing type, and the like to the learning model.

Note that the learning model is generated by performing learning using supervised data in a learning phase, in advance.

Also, a learning model generated based on machine learning other than SVM may also be applied to the emotion estimation unit 16. For example, it is conceivable to use a neural network or a decision tree as the machine learning other than SVM.

Also, in step A6, the estimation unit 3 may also estimate the state of the vocal tract and the state of the respiratory tract using the acoustic characteristic information, and estimate the face expression of a subject using the estimated states of the vocal tract and the respiratory tract. In this case, a face expression such as "sober face" is added, as shown in FIG. 8.

Subsequently, upon acquiring the information indicating the emotion from the emotion estimation unit 16, the output information generation unit 13 generates output information based on the information (step A7). Furthermore, the output information generation unit 13 transmits the output information to the output apparatus 30. Subsequently, the output apparatus 30 outputs the emotion of the subject based on the output information (step A8).

Effects of Example Embodiment

As described above, according to the example embodiment, acoustic characteristic information such as an impulse response h(t) or a transfer function H(z) is generated using an acoustic signal x(t) output to the ear canal of a target user and an echo signal y(t) reflecting the states of organs inside the body. Therefore, the states of organs inside the body can be estimated from the acoustic characteristic information, and as a result, the emotion of a subject can be accurately estimated by using the states of organs.

Also, the emotion can be estimated by using the example embodiment, and therefore smooth communication can be realized in conversation over a telephone, conversation with a robot, and the like.

Also, the emotion can be estimated by using the example embodiment, and therefore the disclosure is useful for voice profiling and the like, in fields such as criminal investigation, marketing, and medical.

[Program]

It suffices for a program in the example embodiment of the disclosure to be a program that causes a computer to carry out steps A1 to A8 illustrated in FIG. 9. By installing this program on a computer and executing the program, the emotion estimation apparatus and the emotion estimation method in the example embodiment can be realized. In this case, the processor of the computer functions and performs processing as the generation unit 2, the estimation unit 3 (the calculation unit 14, the state estimation unit 15, and the emotion estimation unit 16), and the output information generation unit 13.

Furthermore, the program in the example embodiment may be executed by a computer system formed from a plurality of computers. In this case, the computers may each function as one of the generation unit 2, the estimation unit 3 (the calculation unit 14, the state estimation unit 15, and the emotion estimation unit 16), and the output information generation unit 13, for example.

[Physical Configuration]

Figure 10:
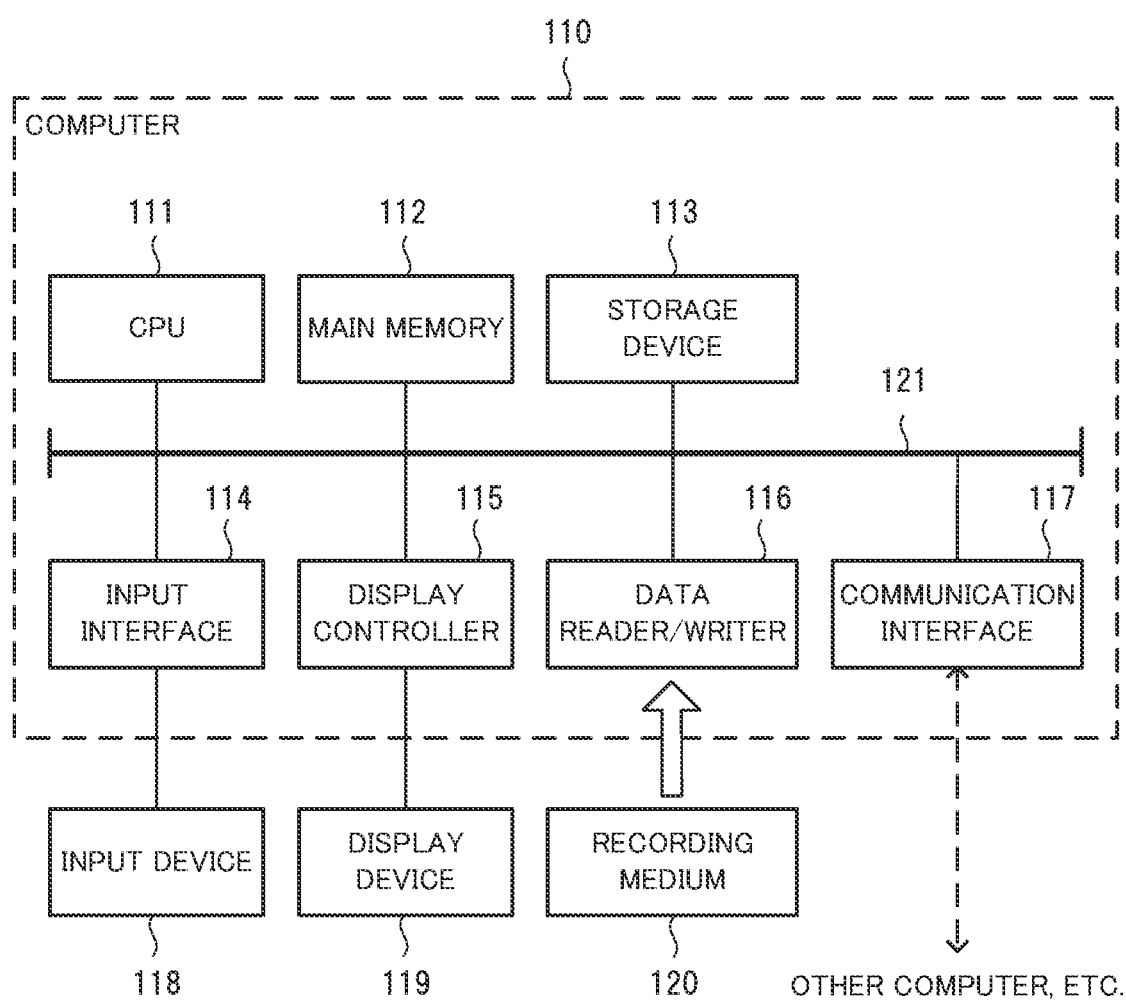
FIG. 10 is a diagram illustrating one example of a computer for realizing the emotion estimation apparatus.

Here, a computer that realizes the emotion estimation apparatus by executing the program in the example embodiment will be described with reference to FIG. 10. FIG. 10 is a block diagram illustrating one example of a computer realizing the emotion estimation apparatus in the example embodiment of the disclosure.

As illustrated in FIG. 10, a computer 110 includes a CPU 111, a main memory 112, a storage device 113, an input interface 114, a display controller 115, a data reader/writer 116, and a communication interface 117. These components are connected via a bus 121 so as to be capable of performing data communication with one another. Note that the computer 110 may include a graphics processing unit (GPU) or a field-programmable gate array (FPGA) in addition to the CPU 111 or in place of the CPU 111.

The CPU 111 loads the program (codes) in the example embodiment, which is stored in the storage device 113, onto the main memory 112, and performs various computations by executing these codes in a predetermined order. The main memory 112 is typically a volatile storage device such as a dynamic random access memory (DRAM). Furthermore, the program in the example embodiment is provided in a state such that the program is stored in a computer readable recording medium 120. Note that the program in the example embodiment may also be a program that is distributed on the Internet, to which the computer 110 is connected via the communication interface 117.

In addition, specific examples of the storage device 113 include semiconductor storage devices such as a flash memory, in addition to hard disk drives. The input interface 114 mediates data transmission between the CPU 111 and input equipment 118 such as a keyboard and a mouse. The display controller 115 is connected to a display device 119, and controls the display performed by the display device 119.

The data reader/writer 116 mediates data transmission between the CPU 111 and the recording medium 120, and executes the reading out of the program from the recording medium 120 and the writing of results of processing in the computer 110 to the recording medium 120. The communication interface 117 mediates data transmission between the CPU 111 and other computers.

Furthermore, specific examples of the recording medium 120 include a general-purpose semiconductor storage device such as a CompactFlash (registered trademark, CF) card or a Secure Digital (SD) card, a magnetic recording medium such as a flexible disk, and an optical recording medium such as a compact disk read-only memory (CD-ROM).

Note that the emotion estimation apparatus 1 in the example embodiment can also be realized by using pieces of hardware corresponding to the respective units, rather than using a computer on which the program is installed. Furthermore, a portion of the emotion estimation apparatus 1 may be realized by using a program, and the remaining portion of the emotion estimation apparatus 1 may be realized by using hardware.

SUPPLEMENTARY NOTE

In relation to the above example embodiment, the following Supplementary notes are further disclosed. While a part of or the entirety of the above-described example embodiment can be expressed by (Supplementary note 1) to (Supplementary note 16) described in the following, the disclosure is not limited to the following description.

Supplementary Note 1

An emotion estimation apparatus comprising:
a generation unit configured to generate acoustic characteristic information indicating an acoustic characteristic using a first acoustic signal output to the ear canal and a second acoustic signal produced by the first acoustic signal echoing inside the body; and
an estimation unit configured to estimate emotion using the acoustic characteristic information.

Supplementary Note 2

The emotion estimation apparatus according to Supplementary note 1, wherein
the estimation unit estimates the state of the vocal tract and the state of the respiratory tract using the acoustic characteristic information, and estimates the emotion using the estimated states of the vocal tract and the respiratory tract.

Supplementary Note 3

The emotion estimation apparatus according to Supplementary note 2, wherein
the estimation unit estimates the state of the vocal tract and the state of the respiratory tract, and estimates expression using the estimated states of the vocal tract and the respiratory tract.

Supplementary Note 4

The emotion estimation apparatus according to Supplementary note 2 or 3, wherein
the estimation unit estimates at least one or more states among whether the mouth is open or closed, whether the vocal cords are open or closed, the place of articulation, and breathing type, and sets the states as the state of the vocal tract and the state of the respiratory tract.

Supplementary Note 5

The emotion estimation apparatus according to Supplementary note 4, wherein
the estimation unit generates resonant frequency information indicating resonant frequencies or spectral shape information indicating a spectral shape using the acoustic characteristic information, and estimates the state of the vocal tract and the state of the respiratory tract using the generated resonant frequency information or spectral shape information.

Supplementary Note 6

The emotion estimation apparatus according to any one of Supplementary notes 1 to 5, further comprising:
an acoustic signal output unit configured to output the first acoustic signal to the ear canal; and
an acoustic signal input unit configured to receive input of the second acoustic signal.

Supplementary Note 7

An emotion estimation method comprising:
(a) a step of generating acoustic characteristic information indicating an acoustic characteristic using a first acoustic signal output to the ear canal and a second acoustic signal produced by the first acoustic signal echoing inside the body; and
(b) a step of estimating emotion using the acoustic characteristic information.

Supplementary Note 8

The emotion estimation method according to Supplementary note 7, wherein
in the (b) step, the state of the vocal tract and the state of the respiratory tract are estimated using the acoustic characteristic information, and the emotion is estimated using the estimated states of the vocal tract and the respiratory tract.

Supplementary Note 9

The emotion estimation method according to Supplementary note 8, wherein
in the (b) step, the state of the vocal tract and the state of the respiratory tract are estimated, and expression is estimated using the estimated states of the vocal tract and the respiratory tract.

Supplementary Note 10

The emotion estimation method according to Supplementary note 8 or 9, wherein
in the (b) step, at least one or more states among whether the mouth is open or closed, whether the vocal cords are open or closed, the place of articulation, and breathing type are estimated and set as the state of the vocal tract and the state of the respiratory tract.

Supplementary Note 11

The emotion estimation method according to Supplementary note 10, wherein
in the (b) step, resonant frequency information indicating resonant frequencies or spectral shape information indicating a spectral shape is generated using the acoustic characteristic information, and the state of the vocal tract and the state of the respiratory tract are estimated using the generated resonant frequency information or spectral shape information.

Supplementary Note 12

A computer readable recording medium that includes recorded thereon, a program including instructions that cause a computer to carry out:
(a) a step of generating acoustic characteristic information indicating an acoustic characteristic using a first acoustic signal output to the ear canal and a second acoustic signal produced by the first acoustic signal echoing inside the body; and
(b) a step of estimating emotion using the acoustic characteristic information.

Supplementary Note 13

The computer readable recording medium according to Supplementary note 12, wherein
in the (b) step, the state of the vocal tract and the state of the respiratory tract are estimated using the acoustic characteristic information, and the emotion is estimated using the estimated states of the vocal tract and the respiratory tract.

Supplementary Note 14

The computer readable recording medium according to Supplementary note 13, wherein
in the (b) step, the state of the vocal tract and the state of the respiratory tract are estimated, and expression is estimated using the estimated states of the vocal tract and the respiratory tract.

Supplementary Note 15

The computer readable recording medium according to Supplementary note 13 or 14, wherein
in the (b) step, at least one or more states among whether the mouth is open or closed, whether the vocal cords are open or closed, the place of articulation, and breathing type are estimated and set as the state of the vocal tract and the state of the respiratory tract.

Supplementary Note 16

The computer readable recording medium according to Supplementary note 15, wherein
in the (b) step, resonant frequency information indicating resonant frequencies or spectral shape information indicating a spectral shape is generated using the acoustic characteristic information, and the state of the vocal tract and the state of the respiratory tract are estimated using the generated resonant frequency information or spectral shape information.

The disclosure has been described with reference to an example embodiment above, but the disclosure is not limited to the above-described example embodiment. Within the scope of the disclosure, various changes that could be understood by a person skilled in the art could be applied to the configurations and details of the disclosure.

INDUSTRIAL APPLICABILITY

As described above, according to the disclosure, the accuracy in estimating emotion can be improved. The disclosure is useful in a filed in which voice profiling or the like is needed. Specifically, the disclosure is useful in fields such as conversation over telephone, conversation with a robot, criminal investigation, marketing, and medical.

REFERENCE SIGNS LIST

1 Emotion estimation apparatus
2 Generation unit
3 Estimation unit
11 Examination electric signal generation unit
12 Echo electric signal acquisition unit
13 Output information generation unit
14 Calculation unit
15 State estimation unit
16 Emotion estimation unit
20 Ear-mounted apparatus
21 Examination sound signal reproduction unit
22 Echo sound signal recording unit
30 Output apparatus
41 Resonant frequency information
42 State estimation information
51 Spectral shape information
52 State estimation information
71 State information
72, 81 Emotion estimation information
110 Computer
111 CPU
112 Main memory
113 Storage device
114 Input interface
115 Display controller
116 Data reader/writer
117 Communication interface
118 Input equipment
119 Display device
120 Recording medium
121 Bus

What is claimed is:

1. An emotion estimation apparatus comprising:
at least one memory storing instructions; and
at least one processor configured to execute the instructions to:
generate acoustic characteristic information indicating an acoustic characteristic using a first acoustic signal output to an ear canal and a second acoustic signal produced by the first acoustic signal echoing inside a body; and
estimate emotion using the acoustic characteristic information.

2. The emotion estimation apparatus according to claim 1, wherein the at least one processor is further configured to execute the instructions to:
estimate a state of a vocal tract and a state of a respiratory tract using the acoustic characteristic information, the emotion estimated using the estimated states of the vocal tract and the respiratory tract.

3. The emotion estimation apparatus according to claim 2, wherein the at least one processor is further configured to execute the instructions to:
estimate expression using the estimated states of the vocal tract and the respiratory tract.

4. The emotion estimation apparatus according to claim 2, wherein the at least one processor is further configured to execute the instructions to:
estimate a state of whether a mouth is open or closed, a state of whether vocal cords are open or closed, a state of a place of articulation, and a state of a breathing type;
set the state of whether the mouth is open or closed, the state of whether the vocal cords are open or closed, and the state of the place of articulation, as the state of the vocal tract; and
set the state of the breathing type as the state of the respiratory tract.

5. The emotion estimation apparatus according to claim 4, wherein the at least one processor is further configured to execute the instructions to:
generate, using the acoustic characteristic information, resonant frequency information indicating resonant frequencies or spectral shape information indicating a spectral shape, the state of the vocal tract and the state of the respiratory tract estimated using the generated resonant frequency information or spectral shape information.

6. The emotion estimation apparatus according to claim 1, wherein the at least one processor is further configured to execute the instructions to:
output the first acoustic signal to the ear canal; and
receive input of the second acoustic signal.

7. An emotion estimation method comprising:
generating acoustic characteristic information indicating an acoustic characteristic using a first acoustic signal output to an ear canal and a second acoustic signal produced by the first acoustic signal echoing inside a body; and
estimating emotion using the acoustic characteristic information.

8. The emotion estimation method according to claim 7, further comprising:
estimating a state of a vocal tract and a state of a respiratory tract using the acoustic characteristic information, the emotion estimated using the estimated states of the vocal tract and the respiratory tract.

9. The emotion estimation method according to claim 8, further comprising:
estimating expression using the estimated states of the vocal tract and the respiratory tract.

10. The emotion estimation method according to claim 8, further comprising:
estimating a state of whether a mouth is open or closed, a state of whether vocal cords are open or closed, a state of a place of articulation, and a state of a breathing typed;
set the state of whether the mouth is open or closed, the state of whether the vocal cords are open or closed, and the state of the place of articulation, as the state of the vocal tract; and
set the state of the breathing type as the state of the respiratory tract.

11. The emotion estimation method according to claim 10, further comprising:
generating, using the acoustic characteristic information, resonant frequency information indicating resonant frequencies or spectral shape information indicating a spectral shape, the state of the vocal tract and the state of the respiratory tract estimated using the generated resonant frequency information or spectral shape information.

12. A non-transitory computer readable recording medium that includes a program recorded thereon, the program including instructions that cause a computer to carry out:
generating acoustic characteristic information indicating an acoustic characteristic using a first acoustic signal output to an ear canal and a second acoustic signal produced by the first acoustic signal echoing inside a body; and
estimating emotion using the acoustic characteristic information.

13. The non-transitory computer readable recording medium according to claim 12, wherein the program further includes instructions that cause the computer to carry out:
estimating a state of a vocal tract and a state of a respiratory tract using the acoustic characteristic information, the emotion estimated using the estimated states of the vocal tract and the respiratory tract.

14. The non-transitory computer readable recording medium according to claim 13, wherein the program further includes instructions that cause the computer to carry out:
estimating expression using the estimated states of the vocal tract and the respiratory tract.

15. The non-transitory computer readable recording medium according to claim 13, wherein the program further includes instructions that cause the computer to carry out:
estimating a state of whether a mouth is open or closed, a state of whether vocal cords are open or closed, a state of a place of articulation, and a state of a breathing type;
setting the state of whether the mouth is open or closed, the state of whether the vocal cords are open or closed, and the state of the place of articulation, as the state of the vocal tract; and
setting the state of the breathing type as the state of the respiratory tract.

16. The non-transitory computer readable recording medium according to claim 15, wherein the program further includes instructions that cause the computer to carry out:
generating, using the acoustic characteristic information, resonant frequency information indicating resonant frequencies or spectral shape information indicating a spectral shape, the state of the vocal tract and the state of the respiratory tract estimated using the generated resonant frequency information or spectral shape information.

\* \* \* \* \*